US007044981B2

(12) United States Patent
Liu et al.

(10) Patent No.: US 7,044,981 B2
(45) Date of Patent: May 16, 2006

(54) URETERAL STENT CONFIGURED FOR IMPROVED PATIENT COMFORT AND AFTERCARE

(75) Inventors: Clifford M. Liu, Randolph, MA (US); Jianmin E. Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 135 days.

(21) Appl. No.: 10/348,715

(22) Filed: Jan. 22, 2003

(65) Prior Publication Data

US 2004/0143209 A1 Jul. 22, 2004

(51) Int. Cl.
*A61F 2/04* (2006.01)

(52) U.S. Cl. .............................. 623/23.66; 623/23.68; 623/23.7; 604/8

(58) Field of Classification Search ............ 623/23.64, 623/23.65, 23.66, 23.68, 23.69, 23.7, 23.67; 604/8
See application file for complete search history.

(56) References Cited

U.S. PATENT DOCUMENTS

| | | | |
|---|---|---|---|
| 4,531,933 A | 7/1985 | Norton et al. | 604/8 |
| 4,610,657 A | 9/1986 | Densow | 604/8 |
| 4,643,716 A | 2/1987 | Drach | 604/8 |
| 4,671,795 A | 6/1987 | Mulchin | 604/281 |
| 4,713,049 A | 12/1987 | Carter | 604/8 |
| 4,790,810 A | 12/1988 | Pugh, Jr. et al. | 604/8 |
| 4,813,925 A * | 3/1989 | Anderson et al. | 604/8 |
| 4,820,298 A | 4/1989 | Leveen et al. | 623/1 |
| 4,874,360 A | 10/1989 | Goldberg et al. | 604/8 |
| 5,019,102 A | 5/1991 | Hoene | 623/12 |
| 5,116,309 A | 5/1992 | Coll | 604/8 |
| 5,141,502 A * | 8/1992 | Macaluso, Jr. | 604/528 |
| 5,221,253 A | 6/1993 | Coll | 604/8 |
| 5,246,446 A | 9/1993 | Zweig | 606/119 |
| 5,401,257 A | 3/1995 | Chevalier, Jr. et al. | 604/265 |
| 5,514,176 A | 5/1996 | Bosley, Jr. | 623/1 |
| 5,647,843 A | 7/1997 | Mesrobian et al. | 604/8 |
| 5,681,274 A | 10/1997 | Perkins et al. | 604/8 |
| 5,769,812 A | 6/1998 | Stevens et al. | 604/4 |
| 5,795,319 A * | 8/1998 | Ali | 604/8 |
| 5,911,710 A | 6/1999 | Barry et al. | 604/249 |
| 5,919,183 A | 7/1999 | Field | 604/530 |
| 5,938,653 A | 8/1999 | Pepin | 604/527 |
| 6,332,892 B1 | 12/2001 | Desmond, III et al. | 623/1.15 |

(Continued)

FOREIGN PATENT DOCUMENTS

WO  WO 01/91668 A1  12/2001

OTHER PUBLICATIONS

Hal K. Mardis, et al., "Ureteral Stents," *Urologic Clinics of North America.* vol. 15, No. 3, Aug. 1988, pp. 471-479.

(Continued)

*Primary Examiner*—Corrine McDermott
*Assistant Examiner*—Thomas J Sweet (57) ABSTRACT

A ureteral stent is configured for improved patient comfort and aftercare. The stent can have one or more of the following features: a distal portion with a somewhat flattened, non-circular cross-section that provides reduced irritation and elimination of urine reflux; a proximal portion with a helical coil shape that allows self-anchoring of the stent below the kidney; and a portion along the body of the stent having a coil shape that allows self-adjustment of the stent with ureteral movement.

38 Claims, 4 Drawing Sheets

U.S. PATENT DOCUMENTS

| | | | |
|---|---|---|---|
| 6,620,202 B1 * | 9/2003 | Bottcher et al. | 623/23.7 |
| 2002/0173754 A1 * | 11/2002 | Whitmore | 604/264 |
| 2003/0171708 A1 * | 9/2003 | Segura et al. | 604/8 |
| 2003/0199986 A1 * | 10/2003 | McWeeney et al. | 623/23.7 |
| 2004/0087886 A1 * | 5/2004 | Gellman | 604/8 |

OTHER PUBLICATIONS

International Search Report for PCT Application No. US2004/001427, filed Jan. 21, 2004, 7 pages.

* cited by examiner

URETERAL STENT CONFIGURED FOR IMPROVED PATIENT COMFORT AND AFTERCARE

FIELD OF THE INVENTION

The invention relates generally to stents; more particularly, the invention relates to ureteral stents.

BACKGROUND OF THE INVENTION

A ureter is a tubular passageway in the body that conveys urine from a kidney to a bladder. Blockages of the ureter may cause hydronephrosis, a condition characterized by damming of urine in the kidneys, resulting in swelling and inflammation of the upper urinary tract and the kidneys. This may lead to kidney dysfunction and eventual necrosis. Ureteral blockages, also called ureteral strictures, may be congenital or acquired. Acquired blockages may be caused by disease, injury, kidney stones, and tumors. Both congenital and acquired blockages generally require medical intervention, for example, the use of ureteral stents.

Ureteral stents are used to facilitate urinary drainage from the kidney to the bladder in patients having a ureteral obstruction or injury, or to protect the integrity of the ureter in a variety of surgical manipulations. Ureteral stents are typically about 30-cm long, hollow catheter-like devices composed of a polymer and placed within the ureter with the proximal end residing in the kidney and the distal end in the bladder. Ureteral stents function by channeling the flow of urine from the kidney to the bladder. One or both ends of a ureteral stent may be coiled in a pigtail shape to prevent the upward and/or downward migration of the stent due to patient movement. The ureter may stretch up to 5 cm in either direction during a patient's normal bodily movements, such as movement during breathing. If the stent is not sufficiently anchored, this may result in stent migration and displacement. Also, a stent may cause tissue irritation due to the relative movement between the stent and the ureter during natural stretching of the ureter, even when the stent is properly anchored. A typical semi-rigid, anchored stent is unable to adjust for the natural extension and contraction of the ureter during bodily movements, resulting in pressure and irritation of the ureter and surrounding tissue.

Regions of tissue most vulnerable to stent-induced irritation include the kidney, the renal pelvis, the sensitive bladder tissue in the trigonal region, and the tissue of the ureteral vesical junction leading into the bladder. Irritation may be caused by the static or dynamic contact of the semi-rigid stent with sensitive tissues of the body, such as the kidney and the renal pelvis. Chronic trigonal tissue irritation may result from contact of tissue by the bladder-anchoring features of the stent, for example, pigtails at the stent ends. Irritation problems are of concern regardless of the duration of use of the stent; however, irritation is of particular concern where use of a stent is required over a long period of time.

Another problem associated with ureteral stents is urine reflux and pain during urine voiding. On the initiation of voiding, the bladder wall muscles contract causing the pressure inside the bladder to increase. Because a typical ureteral stent holds the ureteral orifice open, increased bladder pressure during voiding is transmitted to the kidney through the stent, causing urine reflux and flank pain.

SUMMARY OF THE INVENTION

The invention provides a ureteral stent configured to address a variety of sources of irritation associated with the use of conventional ureteral stents. These irritations include, for example, irritation in the trigonal region of the bladder due to semi-rigid stent contact with bladder mucosa, ureteral vesical junction irritation caused by extension of this region beyond a typical relaxation conformation, pain in the kidney and/or renal pelvis due to the presence therein of part of a semi-rigid stent, and flank pain associated with urine reflux during voiding of the bladder.

The invention features a stent that addresses these sources of irritation by including one or more of the following features: a portion at the distal end having a non-circular cross-section; a proximal portion having a helical coil shape configured to allow anchoring of the stent below the kidney and at or below the renal pelvis; and a portion having an irregular coil shape to allow self-adjustment of the stent with ureteral movement.

In one embodiment, the distal portion of the stent includes a section of hollow tube with a non-circular (e.g., somewhat flattened) profile. The non-circular profile is intended to more closely follow the contour of the intramural tunnel and ureteral vesical junction than does a circular profile. Extension or widening of the cross-section of the ureteral vesical junction due to the presence of the stent is minimized. Thus, there is less irritation caused by the stent at the ureteral vesical junction. The non-circular-profile section of the stent also provides a more flexible, less rigid distal end portion that eases pain and irritation, for example, in the trigonal region of the bladder.

The non-circular-profile section of the stent also provides for the reduction or elimination of urine reflux from the bladder to the kidney during voiding, thereby preventing the associated flank pain. Pressure external to the stent at the non-circular-profile section of the stent collapses the stent shut during voiding of the bladder and prevents reflux of urine to the kidney. After voiding, the stent opens again upon resumption of a normal bladder pressure. The non-circular-profile section of the stent may be made even more flexible and collapsible by the use of a thinner wall thickness in this section. In an embodiment, the distal portion of the stent is anchored in the bladder by a pigtail-shaped end portion, at least part of which has a non-circular cross-section to allow reduced irritation in the bladder and in the urinary vesical junction region.

In another embodiment, the ureteral stent has a proximal portion configured to self-anchor inside an upper portion of the ureter, at or below the renal pelvis, to minimize or eliminate stent irritation in the kidney and/or the sensitive renal pelvis region. In one embodiment, a substantially three-dimensional helical coil shape of sufficiently large helix diameter provides an anchor inside the upper portion of the ureter. By anchoring the stent below the kidney, irritation is minimized in the sensitive renal pelvis region.

Another embodiment provides a stent with a portion forming an irregular helical coil shape to enable the stent to self-adjust with patient movement, thereby reducing irritation due to normal stretching and conformational change of the ureter. The irregular helical coil shape provides a self-adjusting reserve of stent length to allow for stent elongation, contraction, and other conformation change caused by movement of the ureter. The irregular helical coil shape may also provide an additional source of support for the stent within the ureter. In one embodiment, a stent has an irregular helical coil shape along its length, as well as a proximal end portion having a regular helical shape for anchoring the stent below the kidney. The portion of the stent having an irregular helical coil shape may be configured with sufficient helix diameter and height of helix extension so that (1) the proximal portion of the stent is more stably anchored below the kidney, and (2) the stent self-adjusts by elongating and contracting with patient movement. In one embodiment, the irregular helical coil shape has an increasing height of helix extension—fewer turns per unit length—toward the distal portion of the stent near the bladder. The irregular nature of the helical coil shape in this embodiment better follows the anatomy of the ureter than would a regular helical coil shape, and provides reduced stent weight, reduced pressure against ureteral tissue, and reduced irritation to the local tissue without compromising the self-anchoring ability of the stent. In an alternative embodiment, the stent has a portion forming a substantially regular helical coil shape to enable the stent to self-adjust with patient movement.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 2, FIG. 2-1, and FIG. 2—2 depict the ureteral stent of FIG. 1, together with insets illustrating cross-sections at two locations along the body of the stent.

DETAILED DESCRIPTION

The invention provides a ureteral stent configured for improved patient comfort and aftercare. In one embodiment, the stent has a distal portion with a somewhat flattened, non-circular cross-section, thereby providing a more flexible, less rigid, self-aligning lumen in the sensitive trigonal region of the bladder. In another embodiment, the stent features a proximal portion with a helical coil shape to allow self-anchoring of the stent below the kidney, at or below the renal pelvis. Furthermore, one embodiment includes a stent with a portion along its length having an irregular coil shape to allow self-adjustment of the stent with ureteral movement. Other embodiments of the invention include stents with various combinations of the aforementioned features.

Additionally, the invention provides a method of self-adjusting the effective length of a ureteral stent to compensate for patient movement, thereby providing improved patient comfort. An embodiment of the method includes providing a ureteral stent with a portion of its length having an irregular coil shape, anchoring the proximal portion of the stent inside the upper portion of the ureter below the kidney, and allowing the stent to self-adjust in response to patient movement. Patient movement, such as movement during breathing, causes the length of the stent to expand or contract in response to the natural movement of the ureter. Anchoring the stent below the kidney and at or below the renal pelvis provides increased comfort and reduced irritation to the kidney and/or the renal pelvis. The stent used in this method may have any combination of the stent features described herein.

Ureteral stents of the present invention are used, for example, to facilitate urinary drainage from the kidney to the bladder in patients having ureteral obstructions or injuries, or to protect the integrity of the ureter in a variety of surgical manipulations. A patient may undergo either short-term or long-term ureteral stenting. Short term stenting generally lasts up to a period of a weeks, and long-term stenting may last for a period of months or years. In addition to facilitating urinary draining through obstructed ureters, stenting may be used as an adjunct to open surgical procedures of the urinary tract to provide a mold around which healing can occur, or to divert the urinary flow away from areas of leakage. Other uses of stents of the present invention include, for example, maintaining the functionality of ureters following balloon dilation or incision of ureteral strictures, manipulating or preventing kidney stone migration prior to treatment, and making ureters more easily identifiable during difficult surgical procedures. Additionally, ureteral stents of the present invention may be used in those with active kidney infection or with markedly diseased, intolerant bladders, such as bladders damaged from radiation therapy, or bladders invaded by adjacent neoplasm.

Figure 1:
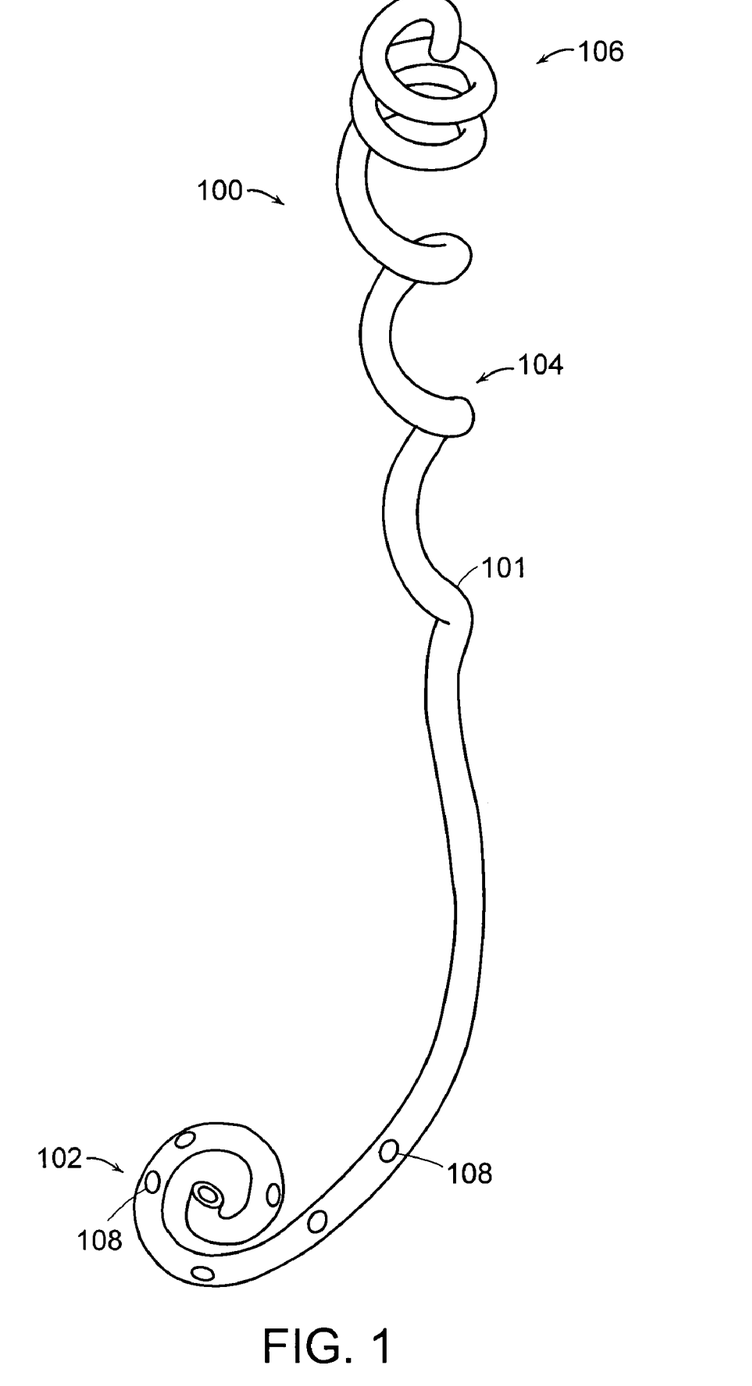
FIG. 1 depicts an embodiment of a ureteral stent of the invention.

FIG. 1 depicts an embodiment of a ureteral stent 100 of the invention. The stent 100 of FIG. 1 includes an elongated, substantially hollow body 101 having a distal portion 102 with a somewhat flattened, non-circular cross-section, a proximal portion 106 with a helical coil shape to allow self-anchoring of the stent below the kidney and at or below the renal pelvis, and a portion along the body of the stent 104 having an irregular coil shape to allow the stent to self-adjust with ureteral movement. As used herein with regard to a ureteral stent, the term "proximal" means nearer to or more associated with the kidney or upper ureter, and the term "distal" means nearer to or more associated with the bladder. The helical coil shape of the proximal portion 106 depicted in FIG. 1 makes about 2 complete turns. In other embodiments, the helical coil shape makes from about 1 turn to about 6 turns or more. Small holes 108 are shown along the distal portion 102 of the stent 100 of FIG. 1. These small openings may be located anywhere along the stent to enhance urinary drainage. The stent body 101 is substantially hollow and allows insertion and removal of a radiopoaqie wire used, for example, to implant the stent. The stent 100 includes two self-anchoring ends—a regular helical coil at the proximal end 106, and a spiral "pigtail" retention feature at the distal end 102. The pigtail shown at the distal end 102 in FIG. 1 is a planar spiral coil formed with a multiplicity of turns wound concentrically, substantially within the same plane. Other retention features may be used at the distal end in place of the pigtail shown, including, for example, a double-J, a double-four, or other coiled retention feature.

Figure 2:
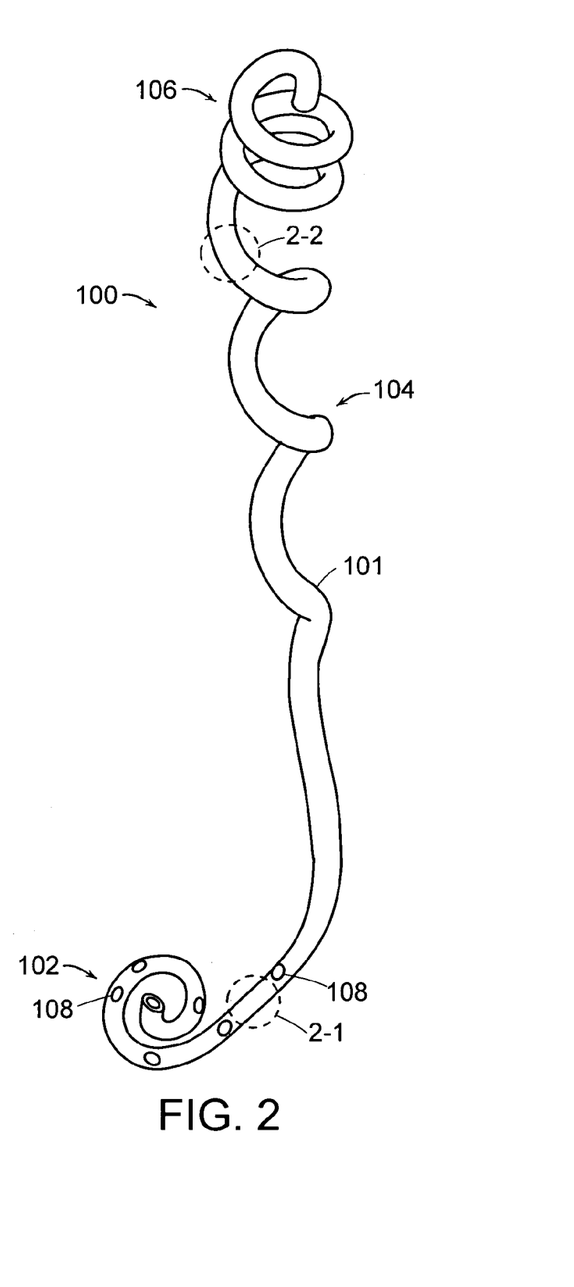

FIG. 2, FIG. 2-1, and FIG. 2—2 depict the uretral stent of FIG. 1, together with insets illustrating cross-sections at two locations along the body of the stent. FIG. 2—2 is an inset illustrating the normal, circular cross-section of the lumen along at least part of the proximal portion 106 of the stent 100. FIG. 2-1 is an inset illustrating the flattened, non-circular cross-section of the lumen part of the distal portion 102 of the stent 100. Here, the two-dimensional profile 202 of the lumen at the distal portion 102 is substantially elliptical in shape, and has a substantially elliptical cross-section with a major axis dimension $d_1$ greater than the minor axis dimension d2. The profile 202 need not be elliptical. In another embodiment, the profile 202 is simply flattened such that its length along one axis is greater than its length along the other axis. Thus, the profile 202 of the distal portion 102 can have an outer perimeter having a non-circular cross-section and/or an inner perimeter having a non-circular cross-section. In one embodiment, the entire lower, distal portion of the stent has a non-circular cross-section. In another embodiment, the stent has a non-circular cross-section only in part of the distal portion of the stent that contacts the ureteral vesical junction.

Figure 3:
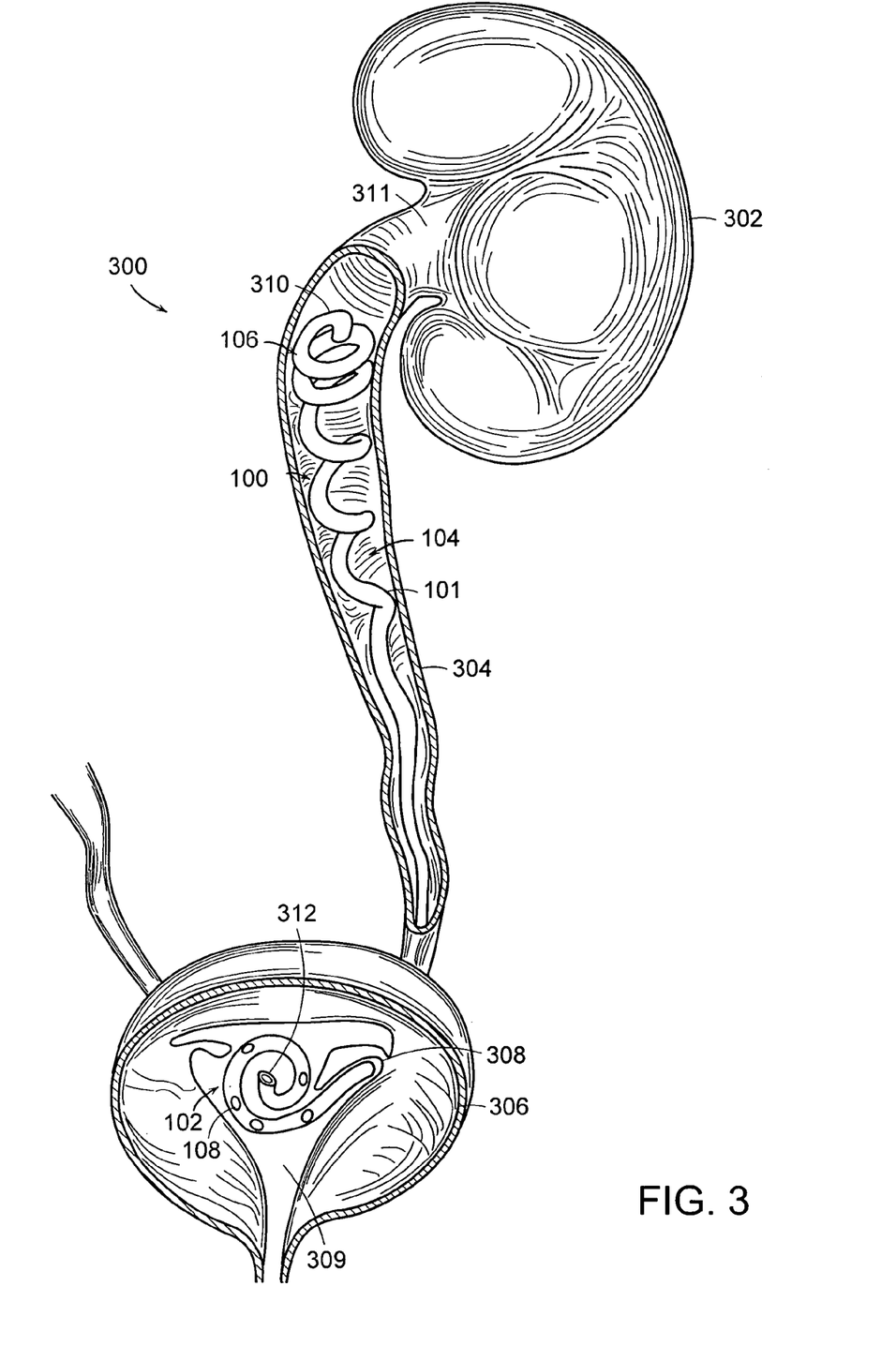
FIG. 3 depicts the ureteral stent of FIGS. 1 and 2 as positioned in a ureter with a proximal portion anchored inside an upper portion of the ureter, below the kidney, and with a distal portion anchored inside the bladder.

FIG. 3 depicts the ureteral stent 100 of FIGS. 1 and 2 as positioned in a ureter 304 with a proximal portion 106 anchored inside an upper portion of the ureter 304 below the kidney 302 such that the upper end 310 of the stent 100 is located below the renal pelvis 311. Alternatively, the upper end 310 of the stent 100 could be located at the renal pelvis 311, but still below the kidney 302. The stent 100 in FIG. 3 has a distal portion 102, part of which is anchored inside the bladder 306 such that the lower end 312 of the stent 100 is located within the bladder 306.

Figure 21:
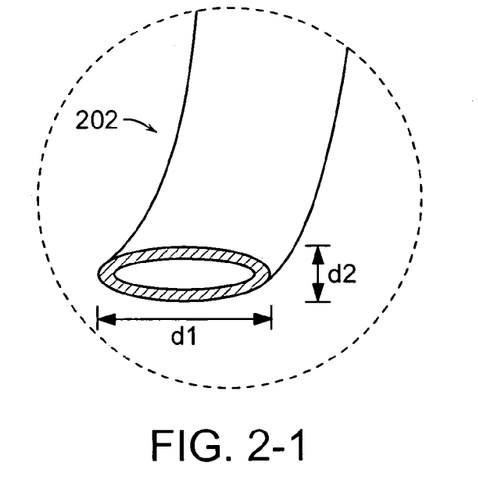
Figure 22:
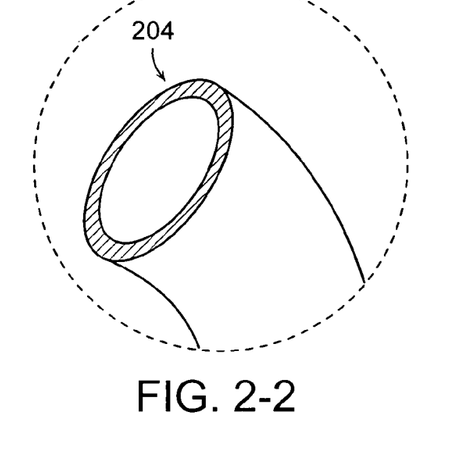

FIG. 3 shows that the flattened profile 202 of the distal portion 102 of the stent 100, highlighted in the inset FIG. 2-1, more closely follows the contour of the ureteral vesical junction 308 than does a circular profile. Since extension or widening of the cross-section of the ureteral vesical junction 308 is minimized, there is less irritation caused by the stent 100 in this area. The flattened section of the stent 100 along the distal portion 102 also provides for a more flexible, less rigid retention feature at the end of the distal portion 102. This reduces pain and irritation associated with the sensitive trigonal region 309 of the bladder.

The flattened section along the distal portion 102 of the stent 100 also provides for the elimination of urine reflux from the bladder 306 to the kidney 302 during voiding, thereby preventing the associated flank pain. During voiding, the pressure in the bladder 306 increases. Pressure external to both the stent 100 at the flattened section and to the bladder wall at the ureteral vesical junction 308 collapses the stent 100 shut at the flattened section during voiding of the bladder 306 and prevents reflux of urine up to the kidney 302. After voiding, the stent 100 opens again, upon resumption of a lower pressure in the bladder 306.

The flattened section of the distal portion 102 of the stent 100 also allows for self-alignment of the stent within the lower ureter 304. If, upon implantation, the stent 100 is not properly aligned such that the wide part of the profile of the flattened portion of the stent 100 aligns with the wide part of the profile of the ureter 304 along the ureteral vesical junction 308, natural movement of the ureter will cause the stent to self-align.

FIG. 3 shows the stent 100 configured with a helical coil at the proximal end 106 with sufficient helical diameter to contact the inner wall of the upper ureter, thereby allowing self-anchoring within the upper portion of the ureter 304, below the kidney 302 and below the renal pelvis 311. Stent irritation in the kidney 302 and the sensitive renal pelvis region 311 normally associated with ureteral stents is minimized since the stent does not extend into these regions. In one embodiment, self-anchoring the proximal end may include adjustably self-anchoring the proximal end inside the upper ureter below the kidney to allow some limited movement of the end of the stent within the ureter, since it may be desirable for purposes of increased patient comfort, for example, to allow some kinds of patient movement to shift the proximal end of the stent along the ureter. Additional anchoring support in the ureter 304 is provided by the irregular helical coil shape 104 along the body 101 of the stent, which is shown in FIG. 3 winding down along the inner wall of the ureter 304. Here, the irregular coil shape 104 is shown with sufficient helix diameter and height of helix extension so that the proximal portion of the stent is more stably anchored in the ureter, below the kidney 302.

Figure 4:
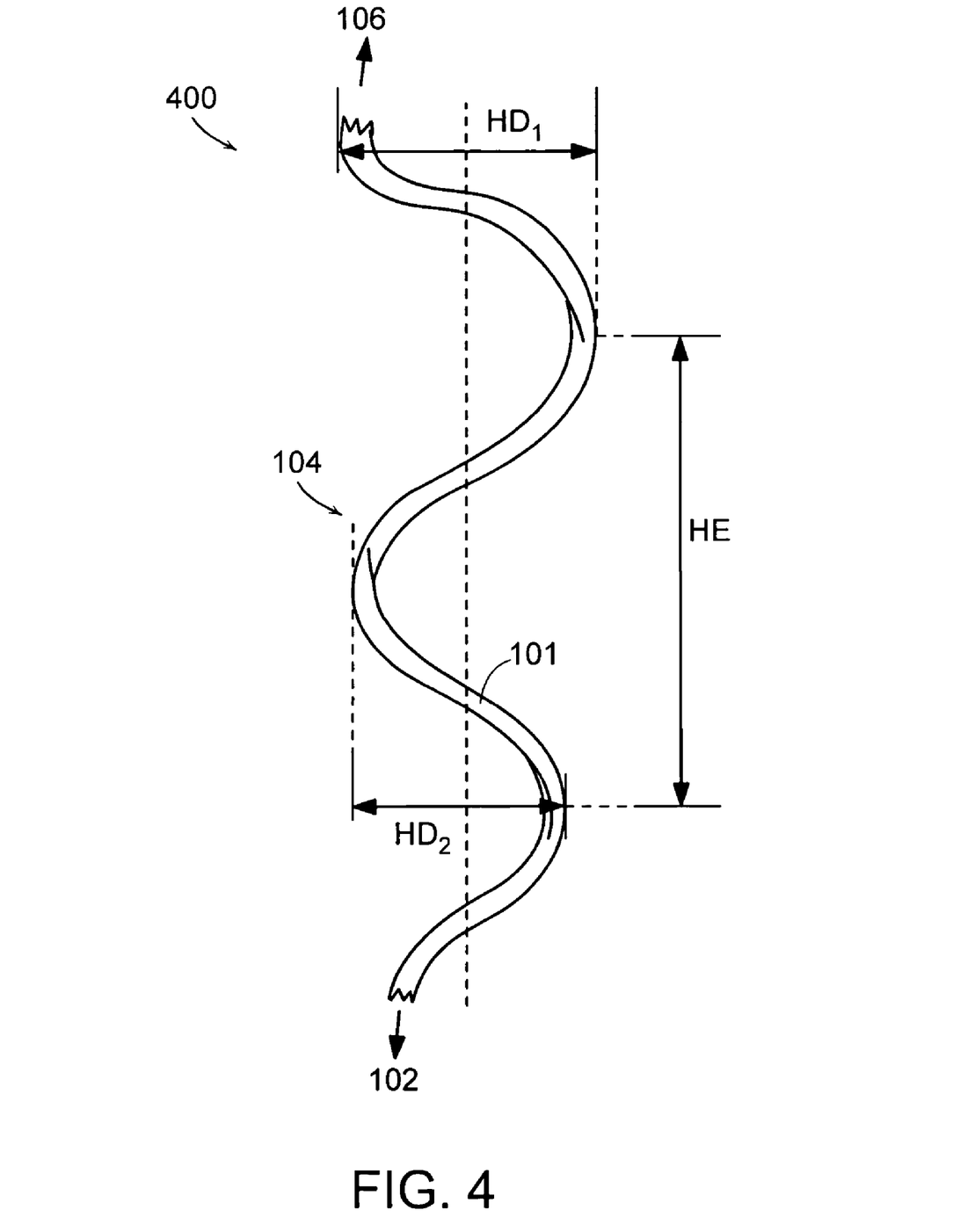
FIG. 4 depicts a helical portion of the body of the stent of FIGS. 1–3 along with geometric indicators.

FIG. 4 depicts an irregular helical portion 400 of the body 101 of the stent 100 of FIGS. 1–3 along with geometric indicators. The irregular coil shape 104 shown in FIG. 3 and FIG. 4 has an increasing height of helix extension, HE, approaching the distal portion 102 of the stent 100 near the bladder 306. The irregular coil shape 104 also has a decreasing helix diameter, HD, approaching the distal portion 102 of the stent 100 near the bladder 306. This is shown in FIG. 4 by $HD_1 > HD_2$. While providing support along the inner wall of the ureter 304 and providing a reserve of stent length to allow for elongation and contraction of the ureter, the configuration shown in FIG. 3 and FIG. 4 also provides for reduced stent weight in the area closer to the bladder 306, thereby reducing pressure in the sensitive trigonal region 309. Other configurations of the irregular coil shape 104 are possible. In one embodiment, part of the stent 100 has a coil shape 104 with alternating portions of high helix extension height (HE) and low helix extension height.

The irregular helical coil shape 104 of the stent 100 shown in FIG. 3 enables self-adjustment of the stent 100 with patient movement. The shape 104 provides a self-adjusting reserve of stent length to allow for elongation and contraction caused by movement of the ureter during normal patient movement. In one embodiment, the reserve length allows the stent 100 to self-adjust with patient movement that stretches the ureter 304 up to about 5 cm. In another embodiment, the reserve length allows the stent 100 to self-adjust with patient movement that stretches the ureter 304 up to about 7 cm.

In one embodiment, the ureteral stent is made of at least one of group of biocompatible plastic materials, including but not limited to polyester-based biocompatible polymers, nylon-based biocompatible polymers, polytetrafluoroethylene (PTFE) polymers, silicone polymers, polyurethane polymers, silicone polyurethane polymers, polyethylene polymers, and thermoplastic polymers, for example. In an embodiment in which it is necessary that the stent undergo significant conformation changes—for example, during implantation—the stent may be constructed from shape memory tubing, such as PERCUFLEX® (Boston Scientific Corporation, Natick, Mass.), C-FLEX® (Xomed-Trease, Inc.), FLEXIMA™, or other polymer material, for example. The stent may have a hydrogel coating, which offers a further reduction of irritation due to contact of the stent with tissue. The stent may be made of a biodegradable polymer, for example, where it is desired that the stent dissolve in-situ after its useful lifetime in the patient.

In an embodiment featuring a stent with a somewhat flattened distal portion, the stent may be created, for example, using single extrusion where one end of the extruded material is round and the other end is flattened. The flattened portion may be achieved, for example, by applying pressure to the heated extrudate. The flat portion provides greater flexibility, more closely resembles the profile of the ureteral vesical junction, allows for self-alignment of the stent, and prevents urine reflux during voiding by collapsing shut upon application of sufficient natural external pressure. In addition to use of a flattened cross-section, the distal portion can be made more flexible by use of a softer material. For example, a softer and more flexible pigtail at the distal end of the stent may be made by bonding a distal portion made of a softer material to the rest of the stent, or by running an interrupted layer extrusion. Heat bonding or adhesive bonding may be accomplished, for example, using methods commonly employed for plastic tubes and catheters.

Typically, in a ureteral application, the non-extended length of the stent in an embodiment of the invention ranges between about 18 cm to about 30 cm. However, in certain embodiments, the stent has a non-extended length less than 18 cm or greater than 30 cm. In one embodiment, the non-extended length of the stent is about 20 cm. The wall thickness of the stent may vary, or it may be substantially uniform. For example, in an embodiment, the wall thickness of the stent at the flattened part of the distal portion is less than the wall thickness elsewhere along the stent in order to provide increased flexibility of the flattened part of the stent, resulting in reduced irritation in the trigonal region and/or ureteral vesical junction. The wall thickness at a given part of the stent is typically between about 0.05 mm and about 0.35 mm, but the wall thickness may be outside this range in some embodiments. In one embodiment, the wall thickness is 0.2 mm. The average outside diameter of the stent is typically between about 1.6 mm and about 3.3 mm, but may be outside this range. In one embodiment, the average outside diameter of the stent is about 2 mm. In one embodiment, the outside diameter of the stent is a value ranging from about French size 6 to about French size 12.

Equivalents

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A ureteral stent for reducing tissue irritation comprising an elongated, substantially hollow body having a proximal portion configured for placement in at least one of a ureter and a kidney of a patient and a distal portion configured for placement in a bladder of the patient, wherein in an unconstrained state at least a first part of said distal portion defines a lumen having an elliptical cross-section and at least a second part of said distal portion forms a substantially spiral shape to retain an end of said stent within the bladder.

2. The stent of claim 1, wherein said first part of said distal portion comprises a section of said stent in contact with a ureteral vesical junction.

3. The stent of claim 1, wherein at least a section of said distal portion is collapsible upon application of a pressure associated with voiding of the bladder.

4. The stent of claim 1, wherein at least a section of said distal portion of said hollow body has a wall thickness that is thinner than the wall thickness of at least a section of said proximal portion.

5. The stent of claim 1, wherein at least a section of said distal portion is configured to self-align within a ureteral vesical junction.

6. The stent of claim 1, wherein said proximal portion defines a lumen having a substantially circular cross-section.

7. The stent of claim 1, wherein said body comprises a hydrogel coating.

8. The stent of claim 1, wherein said body comprises shape memory tubing.

9. The stent of claim 1, wherein said body comprises a biodegradable polymer.

10. The stent of claim 1, wherein said body comprises a plurality of small openings along a length of said body.

11. A ureteral stent comprising an elongated, substantially hollow body having a proximal portion and a distal portion, wherein at least part of said proximal portion forms a substantially helical coil shape that is configured to self-anchor inside an upper portion of a ureter below a kidney, in an unconstrained state at least a portion of said distal portion defines a lumen having a substantially non-circular cross-section.

12. The stent of claim 11, wherein said part of said proximal portion forms a substantially helical coil shape that is configured to self-anchor inside an upper portion of a ureter below a renal pelvis.

13. The stent of claim 11, wherein at least a first part of said distal portion forms a substantially spiral shape to retain an end of said stent within a bladder.

14. A ureteral stent comprising an elongated, substantially hollow body having a proximal portion and a distal portion, said body defining a lumen extending from said proximal portion to said distal portion and configured to convey urine from at least one of a kidney and a ureter of a patient to a bladder of the patient, said proximal portion including a retention member configured to help retain at least a portion of the ureteral stent within the at least one of a kidney and a ureter of the patient, wherein at least a part of said body forms an irregular helical coil shape to enable said body to self-adjust with patient movement.

15. The ureteral stent of claim 14, wherein said irregular helical coil shape has a varying helix diameter along a length of said body.

16. The ureteral stent of claim 14, wherein said irregular helical coil shape has a varying height of helix extension along a length of said body.

17. The ureteral stent of claim 14, wherein said irregular helical coil shape has a decreasing helix diameter and an increasing height of helix extension along a length of said body.

18. The stent of claim 14, wherein said proximal portion forms a substantially helical coil.

19. A ureteral stent comprising an elongated, substantially hollow body having a proximal portion and a distal portion, said body defining a lumen extending from said proximal portion to said distal portion and configured to convey urine from a ureter of a patient to a bladder of the patient, at least part of said proximal portion forms a first substantially helical coil shape configured to self-anchor inside an upper portion of the ureter below a kidney of the patient, and wherein at least part of said body forms a second substantially helical coil shape to enable said body to self-adjust with patient movement.

20. The ureteral stent of claim 19, wherein said part of said body that forms said substantially helical coil shape is of a length sufficient to self-adjust with patient movement that stretches the ureter up to about 5 cm.

21. The ureteral stent of claim 19, wherein said part of said body that forms said substantially helical coil shape is of a length sufficient to self-adjust with patient movement that stretches the ureter up to about 7 cm.

22. The ureteral stent of claim 19, wherein said part of said body forms an irregular helical coil shape to enable said body to self-adjust with patient movement.

23. A ureteral stent comprising an elongated, substantially hollow body having a proximal portion and a distal portion, wherein at least part of said proximal portion forms a substantially helical coil shape that is configured to self-anchor inside an upper portion of a ureter below a kidney, and wherein in an unconstrained state at least part of said distal portion defines a lumen having a substantially non-circular cross-section, and wherein at least part of said body forms a substantially helical coil shape to enable said body to self-adjust with patient movement.

24. A method of self-adjusting a ureteral stent to compensate for patient movement, the method comprising the steps of:
  (a) providing a ureteral stent comprising an elongated, substantially hollow body having a proximal portion and a distal portion, wherein at least part of said body forms a substantially helical coil shape and at least part of said distal portion of said body defines a lumen having a substantially non-circular cross-section;
  (b) anchoring said proximal portion inside an upper portion of a ureter below a kidney; and
  (c) self-adjusting said ureteral stent by allowing patient movement to impart motion on at least a portion of said body in response to a movement of said ureter.

25. The method of claim 24, wherein said patient movement causes an elongation of said body of up to about 5 cm.

26. The method of claim 24, wherein said patient movement causes a change in a conformation of said body.

27. The method of claim 24, wherein said part of said body that forms said substantially helical coil shape is of a length sufficient to self-adjust with patient movement that elongates said body by up to about 5 cm.

28. The method of claim 24, wherein at least part of said proximal portion of said ureteral stent forms a substantially helical coil shape.

29. The method of claim 24, wherein said substantially helical coil shape is an irregular helical coil shape.

30. A ureteral stent comprising an elongated, substantially hollow body having a proximal portion configured for placement in at least one of a ureter and a kidney of a patient and a distal portion defining a lumen and configured for placement in a bladder of the patient, wherein in an unconstrained state at least a first part of said distal portion has an outer perimeter having a non-circular cross-section and at least a second part of said distal portion forms a substantially spiral shape to retain an end of the stent within the bladder.

31. The stent of claim 30, wherein said outer perimeter of said first part of said distal portion has a substantially elliptical cross-section.

32. The stent of claim 30, wherein said outer perimeter of said first part of said distal portion has a cross-section having a shape that is substantially similar to that of a cross-section of a ureteral vesical junction.

33. The stent of claim 30, wherein said at least a portion of said distal portion is collapsible upon application of a pressure associated with voiding of the bladder.

34. The stent of claim 30, wherein said first part of said distal portion defines a lumen with a substantially flattened cross-section.

35. The stent of claim 30, wherein said first part of said distal portion comprises a section of said stent in contact with a ureteral vesical junction.

36. The stent of claim 30, wherein said first part of said distal portion defines a lumen having a substantially non-circular cross-section.

37. A ureteral stent comprising an elongated, substantially hollow body having a proximal portion configured for placement in at least one of a ureter and a kidney of a patient and a distal portion, said distal portion including a first part and a second part, said first part of said distal portion defining a lumen and being configured to contact a ureteral vesical junction, said second part of said distal portion configured for placement in a bladder of the patient, in an unconstrained state an outer perimeter of said first part of said distal portion has a non-circular cross-section.

38. A ureteral stent for reducing tissue irritation comprising an elongated, substantially hollow body having a proximal portion configured for placement in at least one of a ureter and a kidney of a patient and a distal portion configured for placement in a bladder of the patient, in an unconstrained state at least a first part of said distal portion defines a lumen having a substantially non-circular cross-section, at least a section of said distal portion of said hollow body has a wall thickness that is thinner than the wall thickness of at least a section of said proximal portion.

* * * * *